United States Patent [19]
Karl

[11] 3,947,131
[45] Mar. 30, 1976

[54] WINDSHIELD SOIL DETECTOR

[76] Inventor: Gerhard Karl, 8701 Frickenhausen, Uppental 4, Germany

[22] Filed: Nov. 4, 1974

[21] Appl. No.: 520,848

[52] U.S. Cl. .............................................. 356/209
[51] Int. Cl.² ........................................ G01N 21/48
[58] Field of Search .................... 356/209, 134, 135

[56] References Cited
UNITED STATES PATENTS
3,832,567   8/1974   Jacques et al. .................... 307/88.3

*Primary Examiner*—R. V. Rolinec
*Assistant Examiner*—Darwin R. Hostetter
*Attorney, Agent, or Firm*—Webb, Burden, Robinson & Webb

[57] ABSTRACT

A device for indicating the soiling of a sheet of glass or windshield comprising a source that emits light through the windshield onto the soiled surface at the angle of total reflection, a photometer that registers the changes caused in the light returned through the glass as the result of the soiling of the windshield, and an indicating device or signal transmitter connected to the photometer.

6 Claims, 1 Drawing Figure

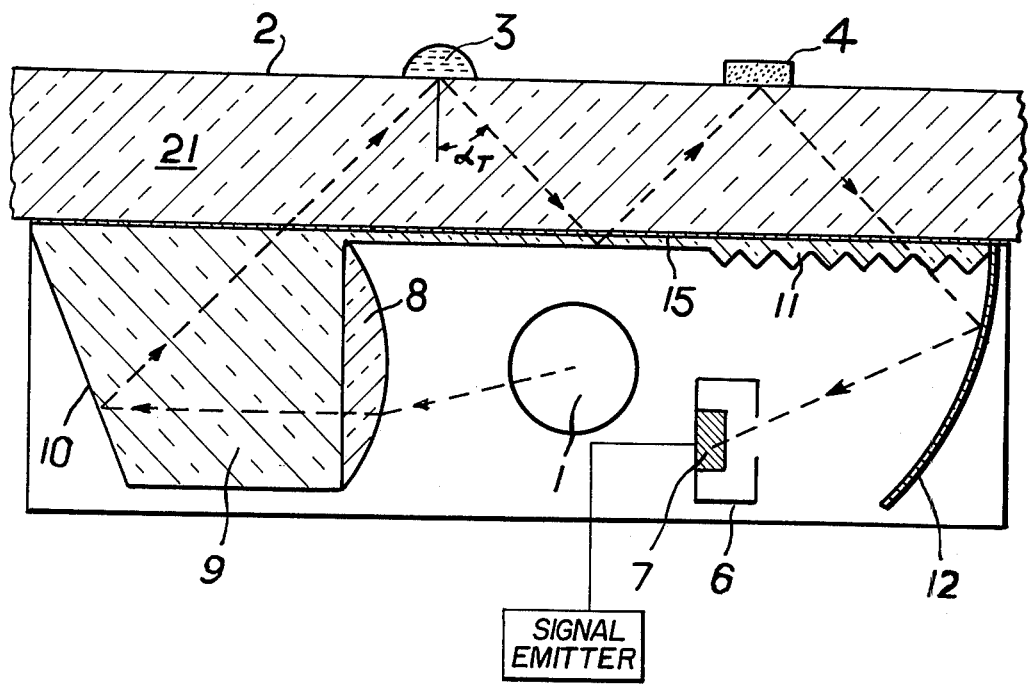

WINDSHIELD SOIL DETECTOR

Up to the present time, no such glass pane soil indicator has been successfully used in daylight. In German Patent application P 21 01 319.4, it is suggested that the light of a light source situated in front of the windshield be sent through the windshield and that the weakness or loss of intensity of the light caused by the soiling of the glass be registered by a photometer disposed behind the windshield pane. But this proposal has the structural drawback that the light source and the photometer must be mounted at two separate places, on both sides of the windshield. It also has the basic drawback that it does not adequately take into consideration the problem of the changing intensity of the outside light. Consequently, in order to compensate for the changing of outside light during daytime and night time, the supplemental proposal is made to set up a second photometer adjacent to the first one in order to eliminate the interference factor of the surrounding brightness by the formation of a differential of the two measured values of the photometers. The above mentioned structural drawback of the separate locations for the light source and the photometers results in a great distance between the two and complicates accurate optical focusing. Furthermore, due to this spatial disposition, the light measuring beam penetrates the windshield pane whose degree of soiling is being measured in only punctiform fashion and does not cover or include the remaining condition of the glass. For these reasons the above mentioned suggestion will probably not be realized in the future.

Another comparable arrangement described in German patent application P 21 37 231.6 bypasses the problem of outside light by being usable only at night, in other words, without the influence of daylight interference. Moreover, this device uses the strong light source of a head light as its source of light, so that in this way it is possible to measure the light sent back from the dirt particles in an indirect manner, since the absence of daylight provides a suitable zero value which allows a critical value to be ascertained. But even the interference caused by the head light of an approaching vehicle requires compensation, which is done by installing time-lag members in series in a relay circuit. This device cannot be used in daylight or with just any desired type of glass pane, such as the windshield of motor vehicles since the latter are never exposed to the light of a strong head light in the daytime and if such a light were constantly turned on during the whole day, it would be an expenditure of energy that would exceed the capacity of an automobile battery.

Briefly, according to this invention, a glass pane soil indicator is secured to the unexposed surface of the pane, A light source and a first optical system direct a beam of light through the unexposed surface to the exposed (soilable) surface at the angle of total reflection. A second optical system is arranged to allow the beam to pass from the pane to a photometer. A signal transmitting device is arranged to produce a signal indicative of the light returned through the pane to the photometer.

It is the object of the invention to create a glass-pane or windshield soiling indicator which is very simple in construction, takes up little space, saves energy and operates in a trouble free manner, an indicator in which the interference factor of changing outside light has been eliminated.

The invention achieves the objects by having the light which is sent from the light source conducted through prismatic devices as it enters or leaves the glass pane, the prismatic devices allowing the light to strike the soiled glass surface at the angle of total reflection.

By using the totally reflecting light proposed by the invention instead of transmitting light, the drawbacks of the two above described prior art methods can be avoided. Outside light which strikes the flat sheet of glass from the outside is always broken at an angle into the interior of the glass, so that no bothersome outside light can reach the photometer. Consequently, no compensation must be made for outside light and the device of the invention can therefore also be used during daylight and under changing outside light conditions. However, if some transparent or non-transparent dirt is present on the surface of the glass, this will affect the total reflection and the photometer can register suitable changes in the light intensity and compare them with the zero value of undisturbed total reflection. When a set given limit value is exceeded, this can be passed on to a signal transmitter connected up at the outlet side.

Advantageously the transparent members of the device and the transparent adhesives for securing the device to the sheet of glass have the same index of refraction as the glass itself, so as to avoid refraction and reflection and thereby to increase the intensity of the light.

The prismatic devices for the entering or departing beam of light may be composed of many small prisms, thus making a flat construction possible.

In order to enlarge the illuminated measuring area on the sheet of glass or windshield, the light emitted from the light source may also be totally reflected in the glass a number of times. Due to this advantageous design it is also possible to arrange the light source and the photometer separately on both sides of the illuminated measured glass area which has been enlarged by multiple total reflection, so that the device of the invention may be divided into two still smaller structural units which may also be glued supplementarily to the inner side of the glass without obstructing the free field of vision. When the device is installed supplementarily no optical adjustment will be necessary since the whole path of the light rays is already preset in the device.

Further features and other objects and advantages of my invention will be described more fully with the aid of the accompanying drawing which is a schematic drawing of one embodiment of my invention emphasizing the optical aspects thereof.

The light issuing from light source 1 is conducted through a focusing optical system 8 (for greater light yield) to a prism 9 and a mirror 10 and is guided to the top surface 2 of the transparent sheet of glass or windshield 21. The totally reflected light emerges from the glass through a prism plate 11 and is focused through an optical system 12 onto photometer 7 with shutter 6. The use of prisms 9 and 11 is necessary because the light must strike top surface 2 of the glass at an angle of total reflection, and should be reflected at the same angle. This cannot be done when a sheet of glass with plane parallel faces is illuminated.

Photometer 7 measures a certain measuring value under interference-free total reflection which represents a good zero or neutral point. If the intensity of the totally reflected light is changed as the result of drops 3 of water or solid dirt particles 4, photometer 7 can determine corresponding new measuring values and pass them on to a signal emitter which is set for a predetermined limit value. When this limit value is exceeded, a signal can be given which will actuate a windshield cleaning device of any desired type. In this connection, it is important that this type of measurement of a totally reflecting beam of light and its changes in intensity takes place completely unaffected by fluctuations in the daylight and furthermore requires a very small light source 1.

In order to prevent refraction and reflection, the transparent parts of the device and the adhesive between the parts have the same index of refraction or a similar one.

In order to enlarge the illuminated surface on the sheet of glass and with the optical system remaining the same, the prisms 9 and 11 are spaced. Then a multiple total reflection can take place in the sheet of glass, thus enlarging the illuminated measuring area on the glass. In this way, the probability of a ray of light that has been totally reflected a number of times striking a drop of water or a particle of dirt and thus interfering with the intensity of the ray of light is substantially increased.

The device is shown approximately four times actual size in the drawing. Therefore, the housing containing the necessary electrical and optical parts is relatively small in its actual size. When the illuminated measuring surface on the glass pane is enlarged and multiple total reflection is utilized, it is possible to split up the device and to make it even smaller, so that the light source 1 is to be contained in one housing and the photometer 7 is to be contained in another housing. These two structural components will then be so small that they will not present the slightest hindrance to the field of vision.

Thus, the described windshield soil indicator consists of only a few small structural components that are scarcely susceptible to trouble, it always operates accurately and is unaffected by changes in outside light, and due to the use of transparent adhesives with the appropriate optical properties, it can very simply be glued to windshields or sheets of glass.

Having thus described my invention with the detail and particularity as required by the Patent Laws, what is desired protected by Letters Patent is set forth in the following claims.

I claim:

1. A glass pane soil indicator for detecting water, dirt or the like on the exposed surface of the pane comprising a portion of said pane having exposed and unexposed surfaces normally free of any substance, a light source, a photometer, means for directing the light from said source through the unexposed surface of the pane to the exposed surface, an optical system for directing light returned through the pane to pass to the photometer, said photometer being arranged to receive only light leaving the exposed pane surface at the angle of total reflection, and means responsive to the output of the photometer for indicating the condition of the exposed glass surface.

2. A glass pane soil indicator according to claim 1 in which said optical system is secured to the pane by a transparent adhesive having the same index of refraction as the pane.

3. A glass pane soil indicator according to claim 1 in which the optical system is comprised of many small prisms.

4. A glass pane soil indicator according to claim 1 in which the directing means and the optical system are spaced such that a single light beam is totally reflected from the exposed and unexposed surfaces at a plurality of points.

5. A glass pane soil indicator according to claim 4 wherein the directing means and the optical system are spaced across the viewing area of the pane from one another such that the measuring area is enlarged by multiple total reflections.

6. A glass pane soil indicator according to claim 1 in which the directing means directs the light to strike the exposed surface at the angle of total reflection.

* * * * *